United States Patent [19]

Patchett et al.

[11] Patent Number: 5,318,901
[45] Date of Patent: Jun. 7, 1994

[54] METHOD FOR THE PRODUCTION OF A MODIFIED "8-AMINO ACID" CYCLOSPORIN DERIVATIVE

[75] Inventors: Arthur A. Patchett, Westfield; Raymond F. White, Englishtown; Robert T. Goegelman, Linden, all of N.J.

[73] Assignee: Merck & Co., Inc., Rahway, N.J.

[21] Appl. No.: 911,433

[22] Filed: Jul. 10, 1992

Related U.S. Application Data

[63] Continuation of Ser. No. 809,213, Dec. 16, 1991, abandoned, which is a continuation of Ser. No. 630,786, Dec. 21, 1990, abandoned, which is a continuation of Ser. No. 311,267, Feb. 16, 1989, abandoned, which is a continuation of Ser. No. 64,674, Jun. 22, 1987, abandoned.

[51] Int. Cl.[5] ............................................. C12P 21/04
[52] U.S. Cl. .................................. 435/71.1; 435/171; 530/317; 530/321; 514/11
[58] Field of Search ............... 435/71.1, 171; 530/317, 530/321; 514/11

[56] References Cited

U.S. PATENT DOCUMENTS

| | | | |
|---|---|---|---|
| 4,102,877 | 7/1978 | Nutt | 530/317 |
| 4,108,985 | 8/1978 | Ruegger et al. | 514/11 |
| 4,117,118 | 9/1978 | Harri et al. | 514/11 |
| 4,210,581 | 7/1980 | Ruegger et al. | 530/321 |
| 4,220,641 | 9/1980 | Traber et al. | 514/11 |
| 4,288,431 | 9/1981 | Traber et al. | 514/11 |
| 4,289,851 | 9/1981 | Traber et al. | 435/71.1 |
| 4,384,996 | 5/1983 | Bollinger et al. | 530/321 |
| 4,396,542 | 8/1983 | Wenger | 530/321 |
| 4,639,434 | 1/1987 | Wenger et al. | 514/11 |
| 4,681,754 | 7/1987 | Siegl | 424/10 |
| 4,703,033 | 10/1987 | Seebach | 514/11 |
| 4,720,483 | 1/1988 | Jansz et al. | 514/11 |
| 4,798,823 | 1/1989 | Witzel | 514/11 |

FOREIGN PATENT DOCUMENTS 056782 7/1982 European Pat. Off. .
194972A 9/1986 European Pat. Off. .

OTHER PUBLICATIONS

J. Kollonitsch, Isr. J. Chem., 17, 53–59 (1978).
R. Wenger, Cyclosporine vol. 1, pp. 14–25 (1983).
R. M. Wenger, Synthesis of Cyclosporine and Analogues; Structural Requirements for Immunosuppressive Activity, Angewandte Chemie 24:2, 77–138 (Feb. 1985).

*Primary Examiner*—Marian Knode
*Attorney, Agent, or Firm*—Curtis C. Panzer; David L. Rose; Joseph F. DiPrima

[57] ABSTRACT

A cyclosporin derivative with incorporated "8-(3-fluoro-D-alanine)" or "8-(2-deutero-3-fluoro-D-alanine)" has been isolated from the fermentation broth of incubating *Tolypocladium inflatum* MF5080 (NRRL 8044) with 3-fluoro-D-alanine or its 2-deuterated isomer respectively. The modified cyclosporins exhibit immunosuppressive properties.

3 Claims, No Drawings

METHOD FOR THE PRODUCTION OF A MODIFIED "8-AMINO ACID" CYCLOSPORIN DERIVATIVE

RELATED U.S. APPLICATION DATA

The instant application is a continuation of U.S. Ser. No. 07/809,213, filed Dec. 16, 1991, now abandoned, which is a continuation of U.S. Ser. No. 07/630,786, filed Dec. 21, 1990, now abandoned, which is a continuation of U.S. Ser. No. 07/311,267, filed Feb. 16, 1989, now abandoned, which is a continuation of U.S. Ser. No. 07/064,674, filed Jun. 22, 1987, now abandoned.

BACKGROUND OF THE INVENTION

Immunoregulatory abnormalities have been s own to exist in a wide variety of "autoimmune" and chronic inflammatory diseases, including systemic lupus erythematosis, chronic rheumatoid arthritis, type 1 diabetes mellitus, inflammatory bowel disease, biliary cirrhosis, uveitis, multiple schlerosis and other disorders such as crohns disease, ulcerative colitis, bullous pemphigoid, sarcoidosis, psoriasis, ichthyosis, and gravies ophthalmopathy. Although the underlying pathogenesis of each of these conditions may be quite different, they have in common the appearance of a variety of autoantibodies and self-reactive lymphocytes. Such self-reactivity may be due, in part, to a loss of the homeostatic controls under which the normal immune system operates.

Similarly, following a bone-marrow or an organ transplantation, the host lymphocytes recognize the foreign tissue antigens and begin to produce antibodies which lead to graft rejection.

The end result of an autoimmune or a rejection process is tissue destruction caused by inflammatory cells and the mediators they release. Antiinflammatory agents such as NSAID's and corticosteroids act principally by blocking the effect or secretion of these mediators but do nothing to modify the immunologic basis of the disease. On the other hand, cytotoxic agents such as cyclophosphamide, act in such a nonspecific fashion that both the normal and autoimmune responses are shut off. Indeed, patients treated with such nonspecific immunosuppressive agents are as likely to succumb from infection as they are from their autoimmune disease.

The cyclosporins are a family of immunosupressive compounds isolated from fermentation broths of various fungal species including *Tolypocladium inflatum* and *Cylindrocarpon lucidum*.

The generic structure of the class of cyclosporins has been established as a cyclic peptide which contains 11 amino acids.

For example, the structure of cyclosporin A was established as a cyclic peptide containing several methylated amino acids and at position 8 this amino acid is D-alanine which has been considered important for the biological activity of cyclosporin.

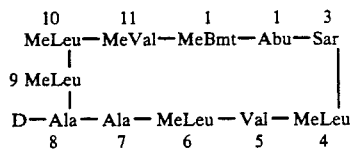

Bmt = (4R)-4-[(E)-2-butenyl]-4-methyl-L-threonine
Me = Methyl
Abu = α-Aminobutyric acid
Val = Valine
Ala = Alanine
MeLeu = N-methyl Leucine
MeVal = Methyl valine
Sar = Sarcosine Generally a cyclosporin such as cyclosporin A is not cytotoxic or myelotoxic. It does not inhibit migration of monocyctes nor does it inhibit granulocytes and macrophage action. Its action is specific and leaves most established immune responses intact. However, it is nephrotoxic and is known to cause the following undesirable side effects:

(1) abnormal liver function;
(2) hirsutism;
(3) gum hypertrophy;
(4) tremor;
(5) neurotoxicity;
(6) hyperaesthesia; and
(7) gastrointestinal discomfort.

Accordingly, an object of the present invention is to provide a less nephrotoxic new cyclosporin derivative which will (1) restore the balance of the help-and-suppression mechanism of the immune system by acting at an earlier point than the anti-inflammatory agents and (2) induce specific long-term transplantation tolerance through a suppressor cell circuit without increasing the body's susceptibility to infection.

Another object of the present invention is to provide pharmaceutical compositions for administering to a patient in need of the treatment the active immunosuppressive agent of the present invention.

Still a further object of this invention is to provide a method of controlling graft rejection, autoimmune and chronic inflammatory diseases by administering a sufficient amount of the novel immunosuppressive agent in a mammalian species in need of such treatment.

Finally, it is the object of this invention to provide processes for the biosynthesis and isolation of the active compound.

DETAILED DESCRIPTION OF THE INVENTION

A. Scope of the Invention

This invention relates to cyclosporin derivatives having 3-fluoro-alanines at the 8-position:

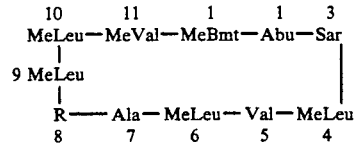

wherein R is 3-fluoro-D-alanine or 2-deutero-3-fluoro-D-alanine. The 3-fluoro-alanine derivatives exhibited immunosuppressive properties similar to cyclosporin A but with lower nephrotoxicity.

B. Biosynthesis Methodology

The modified cyclosporin of this invention has been prepared according to the following fermentation procedure.

EXAMPLE 1

Preparation of
8-(2-deutero-3-fluoro-D-alanine)cyclosporin A

| Culture: Tolypocladium inflatum MF5080, NRRL-8044 | |
|---|---|
| Media: | g/L |
| Slant Medium A | |
| Malt Ext. | 20.0 |
| Yeast Ext. | 4.0 |
| Agar | 20.0 |
| Seed Medium B | |
| Malt Ext. | 70.0 |
| Glucose | 50.0 |
| Culture Medium C | |
| Glucose | 40.0 |
| Caseinpeptone | 10.0 |
| $MgSO_4.7H_2O$ | 0.5 |
| $KH_2PO_4$ | 2.0 |
| $NaNO_3$ | 3.0 |
| KCl | 0.5 |
| $FeSO_4.7H_2O$ | 0.01 |

A lyophile tube was aseptically opened and grown in seed medium B (20 ml in a 250 ml 3-baffle Erlenmeyer flask) for 4 days on a rotary shaker (220 rpm) at 27° C.

This seed was then used to inoculate slants (medium A) for future studies. The slants were incubated at 27° C. for 14 days after which time they were stored at 4° C. until used.

The spores were washed from an entire slant with 5 ml of medium C and used to inoculate a preculture flask (50 ml medium C in a 250 ml Erlenmeyer flask). This preculture was incubated for 5 days at 27° C.

Five ml of the preculture was used to inoculate the production medium (50 ml of medium C and 5 mg/ml of 2-deutero-3-fluoro-D-alanine in a 250 ml Erlenmeyer flask). The filter sterilized 2-deutero-3-fluoro-D-alanine was added (5 mg/ml, final concentration) post-sterilization and prior to inoculation. Forty-four flasks containing a total of 2.2 liters of production medium were incubated 14 to days with agitation (220 rpm) at 27° C. Following incubation, the fermentation broths were extracted by procedures described below in item C.

EXAMPLE 2

Preparation of 8-(3-fluoro-alanine)cyclosporin.

Following essentially the same procedures as described in Example 1 except that the preculture was used to inoculate a production medium of a total volumn of 400 ml containing 5 mg/ml of 3-fluoro-alanine instead of 2-deutero-3-fluoro-alanine, there was obtained the fermentation broth which was extracted by the procedures described below in item C.

C. Extraction Methodology a. The cells were removed from the broth by centrifugation.

b. The clarified broth was extracted 3 times each with 25 ml portions of methylene chloride.

c. The cells were extracted 3 times each with 25 ml portions of acetone.

d. The methylene chloride and acetone extracts were pooled and taken to dryness under vacuum.

e. The residue was solubilized with methanol, dried with anhydrous $Na_2SO_4$, filtered and taken to dryness under vacuum.

f. The samples were submitted for HPLC analysis to determine and isolate the cyclosporin derivatives.

D. HPLC Analysis

Example 1—8-(2-deutero-3-fluoro-alanine)cyclosporin A

Crude extracts were assayed by HPLC chromatography using the following chromatographic system.

| | |
|---|---|
| Solvent: | 80/20 v:v acetonitrile:water |
| Flow rate: | 0.6 mL/min |
| Column: | DuPont Zorbax ODS 4.6 mm × 25 cm maintained at 60° C. |
| Detector: | LDC Spectromonitor III, 210 nm 0.05 AUFS |
| Integrator: | Spectra-Physics SP4100 Computing Integrator |

The concentration of the desired 2-deutero-3-fluro-D-alanine analog of cyclosporin A which has a retention time equal to 92% of the retention time of cyclosporin A, were calculated by dividing the observed area counts by the area counts/mcg of cyclosporin A obtained from an external standard of a known concentration of cyclosporin A.

The extraction residues from four fermentations, representing 2.2 L of broth, were combined in 75 ml of methanol and assayed by HPLC chromatography. The sample which contained 43.1 mg of crude 8-(2-deutro-3-fluoro-D-alanine)-cyclosporin A was labeled A.

Sample A was concentrated to a slightly oily residue. The residue was taken up in 6 ml of 1:1 v:v methylene chloride: methanol. The solution was then chromatographed on a 200 ml column of Pharmacia LH-20, previously equilibriated with methanol. The chromatography was carried out with methanol at a flow rate of 5 ml/min collecting one eight ml fraction followed by 40x5 ml fractions. Fractions 22 through 26 were combined and labeled B, volume 25 ml.

Sample B contained 33.7mg of 8-(2-deutero-3-fluoro-D-alanine)-cyclosporin-A by HPLC analysis.

Sample B was concentrated to dryness and the residue taken up in 1 ml of methanol. This solution was subjected to preparative HPLC chromatography on a DuPont Zorbax ODS column 2.1×25cm maintained at 60° C. using a solvent system of 80/20 v:v acetonitrile:water at a flow rate of 10 ml/min. The effluent stream was monitored at 210 nm using a Gilson Model 116 U.V. detector equipped with a 0.05mm path length cell and a setting of 0.32 AUFS. The U.V. signal was monitored with a Spectra-Physics SP4100 computing integrator and 15 fractions were collected based on the ultra-violet trace. Fraction 9 was labeled C. Fraction 10 was concentrated to dryness and the residue labeled D.

Sample D was dissolved in 0.5 ml of methanol. This solution was subjected to preparative HPLC chromatography on a DuPont Zorbax ODS column 2.1×25 cm maintained at 60° C. using a solvent systems of 80/20 v:v acetonitrile:water at a flow rate of 10 mL/min. The effluent stream was monitored at 226 nm using an LDC Spectromonitor II equipped with a 1 mm path length cell and a setting of 0.32 AUFS. The U.V. signal was monitored with a Spectra-Physics SP4100 computing integrator and 10 fractions were collected based on the ultra-violet trace. Fractions 4 and 5 were selected and combined with Sample C, volume 35 ml, and was labeled E. Sample E contained 20.1 mg of 8-(2-deutero-3-fluoro-D-alanine)-cyclosporin A with an ultra-violet purity of >99% at 226 nm by HPLC analysis. Sample E was concentrated to dryness under high vacuum to yield 20.2 mg of 8-(2-deutero-3- fluoro-D-alanine)-cyclosporin A.

Example 2—8-(3-fluoro-D-alanine)-cyclosporin A

The extraction residue from one 400 ml fermentation was taken up in 1 ml of methylene chloride and the solution chromatographed on a 40 ml column of Pharmacia LH-20 previously equilibriated with methanol. The chromatography was carried out with methanol at a flow rate of 2 ml/min., collecting one ten ml fraction followed by 30×1 ml fractions. Fractions 16 through 27 were selected and combined, based on HPLC analysis. The combined fractions were concentrated to dryness and the residue labeled F.

Sample F was taken up in 250 ml of methanol and subjected to preparative HPLC chromatography on a DuPont Zorbax ODS column 0.94×25 cm maintained at 60° C., Chromatography was carried out with a solvent system of 80:20 v:v actonitrile:water at a flow rate of 2 ml/min. The effuent stream was monitored at 220 nm using an LDC Spectromonitor II equipped with a 1 mm path length cell and a setting 1.28 AUFS. The ulta-violet signal was monitored using a SpectraPhysics SP4100 computing integrator and eleven fractions were collected based on the ultra-violet trace. Fraction 7 contained 3.25mg of 8-(3-fluoro-D-alanine)-cyclosporin-A with an ultra-violet purity of >99% at 210 nm by HPLC analysis. Fraction 7 was concentrated to dryness under high vacuum to yield 3.3 mg of 8-(3-fluoro-D-alanine)-cyclosporin A.

E. Physical Characterization of B-(2-deutero-3-fluoro-D-alanine)-cyclosporin A

Mass spectrum: $(M+H)^+$, m/2 1221, 19 mass units up from the value (1202) was found for cyclosporin A, and is consistent with the substitution of an alanine residue in cyclosporin A by 2-deutero-3-fluoro-D-alanine.

'H NMR Spectrum: The 'H NMR data established the incorporation of the 2-deutero-3-fluoro-D-alanine at the 8-position.

$^{13}$NMR Spectrum:

The spectrum was recorded at 100 MHZ in $CDCl_3$ on a Varian XL-400 spectrometer at ambient room temperature. Chemical shifts are shown relative to TMS at zero ppm using the solvent peak at 77.0 ppm as reference: 10.0, 16.1, 17.0, 18.1, 18.5, 18.8, 20.0, 20.5, 21.2, 21.8, 22.0, 23.6(2×), 23.9(2×), 24.0, 24.2, 24.5, 24.9, 25.0. 25.6, 29.3, 29.88, 29.94, 29.96, 31.2, 31.4, 35.8, 36.0, 36.2, 37.5, 39.2, 39.6, 40.6, 48.75(2×), 48.83, 50.4, 55.3, 55.45, 55.49. 57.6, 57.9, 59.0, 74.8. 81.9d, (J=177.2 Hz)*, 126,2, 129.5, 169.8, 169.9(2×), 170.9 d*, 170.1, 171.1, 171.53, 171.56, 173.4, 173.59, 173.61 ppm.

*These resonances of the 3-fluoro-2-deutero-D-alanine residue are observed as doublets due to coupling with the $^{19}$F nucleas, The $^{13}$C NMR data of 61 carbons is consistent with the molecular formula $C_{62}H_{109}DN_{11}O_{12}F$ on the assumption that the α-carbon of the 3-fluoro-2-deutero-D-alanine residue carrying the deuterium atom is not observed.

F. Utility of the Compounds Within the Scope of the Invention

This invention also relates to a method of treatment for patients suffering from graft rejection after transplantation, autoimmune or chronic inflammatory diseases which involves the administration of a compound of formula (I) as the active constituent.

For the treatment of these conditions and diseases a compound of formula (I) may be administered orally, topically, parenterally, by inhalation spray or rectally in dosage unit formulations containing conventional nontoxic pharmaceutically acceptable carriers, adjuvants and vehicles. The term parenteral as used herein includes subcutaneous injections, intravenous, intramuscular, intrasternal injection or infusion techniques. In addition to the treatment of warmblooded animals such as horses, cattle, sheep, dogs, cats, etc., the compounds of the invention are effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparation. Tablets containing the active ingredient in admixture with non-toxic pharmaceutically acceptable excipients may also be manufactured by known methods. The excipients used may be for example, (1) inert diluents such as calcium carbonate, sodium carbonate, lactose, calcium phosphate or sodium phosphate; (2) granulating and disintegrating agents such as corn starch, or alginic acid; (3) binding agents such as starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,160,452; and 4,265,874 to form osmotic therapeutic tablets for controlled release.

In some cases, formulations for oral use may be in the form of hard gelatin capsules wherein the active ingredient is mixed with an inert solid diluent, for example, calcium carbonate, calcium phosphate or kaolin. They may also be in the form of soft gelatin capsules wherein the active ingredient is mixed with water or an oil medium, for example peanut oil, liquid paraffin, or olive oil.

Aqueous suspensions normally contain the active materials in admixture with excipients suitable for the manufacture of aqueous suspensions. Such excipients may be (1) suspending agents such as sodium carboxymethylcellulose, methylcellulose, hydroxypropylmethylcellulose, sodium alginate, polyvinylpyrrolidone, gum tragacanth and gum acacia;

(2) dispersing or wetting agents which may be
 (a) a naturally-occurring phosphatide such as lecithin,
 (b) a condensation product of an alkylene oxide with a fatty acid, for example, polyoxyethylene stearate,
 (c) a condensation product of ethylene oxide with a long chain aliphatic alcohol, for example, heptadecaethyleneoxycetanol,
 (d) a condensation product of ethylene oxide with a partial ester derived from a fatty acid and a hexitol such as polyoxyethylene sorbitol monooleate, or (e) a condensation product of ethylene oxide with a partial ester derived from a fatty acid and a hexitol anhydride, for example polyoxyethylene sorbitan-monooleate.

The aqueous suspensions may also contain one or more preservatives, for example, ethyl or n-propyl p-hydroxybenzoate; one or more coloring agents; one or more flavoring agents; and one or more sweetening agents such as sucrose or saccharin.

Oily suspension may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide a palatable oral preparation. These compositions may be preserved by the addition of an antioxidant such as ascorbic acid.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example, those sweetening, flavoring and coloring agents described above may also be present.

The pharmaceutical compositions of the invention may also be in the form of oil-in-water emulsions. The oily phase may be a vegetable oil such as olive oil or arachis oils, or a mineral oil such as liquid paraffin or a mixture thereof. Suitable emulsifying agents may be (1) naturally-occurring gums such as gum acacia and gum tragacanth, (2) naturally-occurring phosphatides such as soy bean and lecithin, (3) esters or partial esters derived from fatty acids and hexitol anhydrides, for example, sorbitan monooleate, (4) condensation products of said partial esters with ethylene oxide, for example, polyoxyethylene sorbitan monooleate. The emulsions may also contain sweetening and flavoring agents.

Syrups and elixirs may be formulated with sweetening agents, for example, glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to known methods using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

A compound of (I) may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the immunoregulants are employed.

The amount of active ingredient that may be combined with the carrier materials to produce a single dosage form will vary depending upon the host treated and the particular mode of administration. For example, a formulation intended for the oral administration of humans may contain a therapeutically sufficient amount of active agent compounded with an appropriate and convenient amount of carrier material which may vary from about 5 to about 95 percent of the total composition.

The specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

G. Biological Evidence in Support of Utility of the Compounds Within the Scope of the Invention It has been found that the compounds of formula (I) have immunosuppressive activities and are thereby useful in the treatment of various "autoimmune" and chronic inflammatory diseases. They may also be useful in the prevention of graft rejection or rejection of "donor" organs in transplantation operations. The following tables illustrate and support the utility of the compounds of the present invention:

In this in vitro nephrotoxicity assay, 8-(2-deutero-3-fluoro-D-alanine)-cyclosporin A was less toxic than cyclosporin A over the relatively narrow dose range at which solubility permitted testing.

In Vitro Nephrotoxicity Assay

A sample of 2-deutero-3-fluoro-D-alanine was evaluated in the in vitro nephrotoxicity assay which utilizes freshly prepared proximal tubules from rabbit as the target tissue, and measures changes in $^3$H-leucine incorporation as a parameter of toxicity. The purpose of the assay was to determine the toxicity of the test compounds relative to cyclosporin A. Previous validation of the assay using cephalosporin antibiotics has shown that this assay can accurately predict relative, inherent toxic potential at the cell level. The only assumption that needs to be made is that pharmacokinetic/drug distribution parameters are not substantially different. The utility of the methodology was further demonstrated in a comparison of in vivo and in vitro data on thienamycin analogs which showed that in vitro assay is at least 90% accurate in predicting in vivo nephrotoxicity relative to a reference compound.

Suspensions of tubules were exposed to the test compound at appropriate concentrations for a total of 23 hours, with a $^3$H-leucine pulse being given during the last 3 hours of exposure. Incorporation of leucine was determined per ug protein; the specific activity of each test point was graphed as a percent of control specific activity. In this experiment, we decided to dose with levels of drug which appeared to be out of solution in order to achieve the highest possible dose (assuming that some of the compound would dissolve and equilibrate during the 23 hours exposure). As can be seen in the following table, compound 8-(2-deutero-3-fluoro-D- alanine)cyclosporin A was less toxic than cyclosporin A at dose 30 ug/ml:

| Compound | Dosage | Mean Specific Activity (± standard error) |
|---|---|---|
| Cyclosporin A | 30 μg/ml | 75.1 (10.1) |
| 8-(2-deutero-3-fluoro-D-alanine)-cyclosporin A | " | 92.0 (0.3) |

Based on the data over the limited range tested, and assuming that pharmacokinetic factors are equivalent, it is expected that 8-(2-deutero-3-fluoro-D-alanine)-cyclosporin A to be less nephrotoxic in animals than is cyclosporin A.

What is claimed is:

1. A process for the preparation of a compound of formula (I):

$$
\begin{array}{ccccc}
10 & 11 & 1 & 2 & 3 \\
\text{MeLeu} - \text{MeVal} - \text{MeBmt} - \text{Abu} - \text{Sar} \\
| & & & & | \\
9 \text{ MeLeu} & & & & | \\
| & & & & | \\
\text{R} - \text{Ala} - \text{MeLeu} - \text{Val} - \text{MeLeu} \\
8 & 7 & 6 & 5 & 4
\end{array}
$$

wherein R is 3-fluoro-D-alanine; or 2-deutero-3-fluoro-D-alanine comprising:
(a) culturing *Tolypocladium inflatum* MF5080 (NRRL 8044) in a nutrient medium containing assimilable sources of carbon, nitrogen, inorganic salts and 3-fluoro-D-alanine or 2-deutero-3-fluoro-D-alanine to produce the compound of Formula I; and
(b) extracting and isolating the compound of Formula I.

2. A process for the preparation of a compound of Formula (I)

$$
\begin{array}{ccccc}
10 & 11 & 1 & 2 & 3 \\
\text{MeLeu} - \text{MeVal} - \text{MeBmt} - \text{Abu} - \text{Sar} \\
| & & & & | \\
9 \text{ MeLeu} & & & & | \\
| & & & & | \\
\text{R} - \text{Ala} - \text{MeLeu} - \text{Val} - \text{MeLeu} \\
8 & 7 & 6 & 5 & 4
\end{array}
$$

wherein R is 3-fluoro-D-alanine comprising:
(a) culturing *Tolypocladium inflatum* MF5080 (NRRL 8044) in a nutrient medium containing assimilable sources of carbon, nitrogen, inorganic salts and 3-fluoro-D-alanine to produce the compound of Formula I; and
(b) extracting and isolating the compound of Formula I.

3. A process for the preparation of a compound of Formula (I)

$$
\begin{array}{ccccc}
10 & 11 & 1 & 2 & 3 \\
\text{MeLeu} - \text{MeVal} - \text{MeBmt} - \text{Abu} - \text{Sar} \\
| & & & & | \\
9 \text{ MeLeu} & & & & | \\
| & & & & | \\
\text{R} - \text{Ala} - \text{MeLeu} - \text{Val} - \text{MeLeu} \\
8 & 7 & 6 & 5 & 4
\end{array}
$$

wherein R is 2-deutero-3-fluoro-D-alanine comprising:
(a) culturing *Tolypocladium inflatum* MF5080 (NRRL 8044) in a nutrient medium containing assimilable sources of carbon, nitrogen, inorganic salts and 2-deutero-3-fluoro-D-alanine to produce the compound of Formula I; and
(b) extracting and isolating the compound of Formula I.

* * * * *